United States Patent
Dings et al.

(10) Patent No.: US 8,268,239 B2
(45) Date of Patent: Sep. 18, 2012

(54) METHOD AND APPARATUS FOR STERILIZING CONTACT LENSES

(75) Inventors: Franciscus Cornelius Dings, Eindhoven (NL); Michael Adrianus T. Hompus, Eindhoven (NL); Michiel Paulus A. M. Prinz, Eindhoven (NL); Wilhelmus Godefridus J. P. Swinkels, Eindhoven (NL)

(73) Assignee: OTB Group B.V., Eindhoven (NL)

( * ) Notice: Subject to any disclaimer, the term of this patent is extended or adjusted under 35 U.S.C. 154(b) by 551 days.

(21) Appl. No.: 12/299,428

(22) PCT Filed: May 4, 2007

(86) PCT No.: PCT/NL2007/050196
§ 371 (c)(1),
(2), (4) Date: Feb. 18, 2009

(87) PCT Pub. No.: WO2007/129892
PCT Pub. Date: Nov. 15, 2007

(65) Prior Publication Data
US 2011/0027123 A1 Feb. 3, 2011

(30) Foreign Application Priority Data

May 4, 2006 (NL) ..................................... 1031750

(51) Int. Cl.
*A61L 2/00* (2006.01)
*A61L 2/04* (2006.01)
*A61L 2/18* (2006.01)
*A61L 2/20* (2006.01)
*A61L 9/00* (2006.01)
*A61L 11/00* (2006.01)
*C23F 11/00* (2006.01)

(52) U.S. Cl. .................. 422/25; 422/1; 422/28; 422/31; 422/33; 422/38

(58) Field of Classification Search .................. 422/28, 422/307, 21, 22, 25, 1, 31, 33, 38
See application file for complete search history.

(56) References Cited

U.S. PATENT DOCUMENTS 3,347,155 A * 10/1967 Mencacci ........................ 99/365
4,015,935 A *  4/1977 Andersson et al. ........... 422/297
4,044,226 A     8/1977 Kadlecik et al.
(Continued)

FOREIGN PATENT DOCUMENTS
EP         0281255 A1    9/1988
(Continued)

OTHER PUBLICATIONS

International Search Report issued on Aug. 22, 2007 in International Application No. PCT/NL2007/050196.

*Primary Examiner* — Regina M. Yoo
(74) *Attorney, Agent, or Firm* — Pillsbury Winthrop Shaw Pittman LLP (57) ABSTRACT

A method for sterilizing contact lenses included in a moist environment in a closed package, wherein the package is heated, wherein the heating is carried out by introducing the package into a space which is at superatmospheric pressure or which is adjusted to superatmospheric pressure and which is heated with dry hot air. Further, the invention relates to an apparatus for carrying out such a method.

15 Claims, 5 Drawing Sheets

U.S. PATENT DOCUMENTS

| | | | |
|---|---|---|---|
| 4,116,117 A * | 9/1978 | Bogaard | 99/361 |
| 4,196,225 A * | 4/1980 | Mencacci | 426/523 |
| 4,582,076 A * | 4/1986 | Prat | 134/57 R |
| 4,646,629 A * | 3/1987 | Creed et al. | 99/468 |
| 4,646,650 A * | 3/1987 | Kondo et al. | 104/172.3 |
| 4,674,267 A * | 6/1987 | Szemplenski et al. | 53/432 |
| 4,824,644 A * | 4/1989 | Cox et al. | 422/300 |
| 4,874,580 A * | 10/1989 | Sugisawa et al. | 422/25 |
| 5,422,130 A * | 6/1995 | Fox et al. | 426/234 |
| 5,439,643 A * | 8/1995 | Liebert | 422/25 |
| 5,476,635 A * | 12/1995 | Stoker | 422/26 |
| 5,685,125 A * | 11/1997 | Cattelli et al. | 53/127 |
| 5,882,687 A * | 3/1999 | Park et al. | 424/682 |
| 6,626,087 B2 * | 9/2003 | Roumagnac | 99/330 |
| 2005/0123435 A1 * | 6/2005 | Cutler et al. | 422/1 |
| 2006/0073185 A1 | 4/2006 | Jani et al. | |

FOREIGN PATENT DOCUMENTS

| | | |
|---|---|---|
| WO | 98/30248 A2 | 7/1998 |
| WO | 03/074093 A2 | 9/2003 |
| WO | WO 03/074093 A2 * | 9/2003 |

* cited by examiner

METHOD AND APPARATUS FOR STERILIZING CONTACT LENSES

CROSS REFERENCE TO RELATED APPLICATIONS

This application is a U.S. national stage entry of International Application No. PCT/NL2007/050196, filed on May 4, 2007 which claims priority to The Netherlands Application No. 1031750, filed May 4, 2006. The contents of these applications is incorporated herein by reference.

This invention relates to a method for sterilizing contact lenses, more particularly to a method for sterilizing contact lenses included in a moist environment in a closed package.

It is known from practice to sterilize contact lenses by heating them in an autoclave chamber with steam. That is a slow batch process, which requires a simple control, in that upon raising the temperature in the autoclave space, steam is formed. Upon further raising of the temperature, the pressure in the autoclave space increases automatically under the influence of the steam that is formed therein.

In practice, the prejudice prevails that steam is necessary for rapidly sterilizing products. The steam precipitating on the products, due to the heat of condensation thereby released, provides for a very rapid heat transfer to the products to be sterilized. Moreover, what is automatically accomplished with the known method is that the pressure inside the closed package and the pressure outside of it are substantially equal, so that the packages do not tear.

Especially for packaged contact lenses, however, the use of steam is disadvantageous, because steam is rather corrosive. The generally aluminum foil packages of contact lenses, but also other types of contact lens packages are affected by the steam. Spots appear on them, which adversely affect the fine appearance of the packages.

The object of the invention is to provide a fast and efficient manner of sterilizing packaged contact lenses without the disadvantages described.

The invention is based, for one thing, on the insight that the outside of the package does not need to be sterilized. As long as steam is created in the interior of the package—and this is possible since the environment there is moist—a sterilization of the interior of the package and the lens contained in it can be realized fast. In view of the formation of the steam, what is to be prevented is that the pressure running up in the package leads to the package tearing open.

Based on this insight, the present invention provides a method of the type described in the opening paragraph hereof, which is characterized in that the heating is carried out by introducing the package into a space which is heated with dry hot air.

Owing to the air being dry, no steam is formed outside the package and the fine exterior of the package does not sustain any damage.

Preferably, the pressure in the space outside the package is higher than the vapor pressure of water in the package, at a temperature prevailing in the package, and the temperature of the dry hot air can be such that in the package hot water and possibly steam is generated. The steam is not requisite for the sterilization and the pressure may be higher than the vapor pressure associated with the temperature.

According to a further elaboration of the invention, the space is at a superatmospheric pressure or is adjusted to a superatmospheric pressure. What is prevented by the pressure in the space being maintained superatmospheric is that possible steam formation in the package and the internal pressure thereby running up in the package lead to the package bursting open. Also, the package will not expand much and hence not shrink much afterwards either, so that any imprint on the package will not crease and/or change in appearance.

According to a further elaboration of the invention, the superatmospheric pressure is kept above the pressure prevailing in the package. The pressure prevailing in the package can be derived from the pressure/temperature diagram for steam. The steam/vapor pressure curve of the moisture in the package reflects the pressure prevailing in the package at a particular temperature.

According to a further elaboration of the invention, the pressure is maintained at approximately 4 bar.

According to a further elaboration of the invention, the lens packages are introduced into the space in carriers.

The packages are then preferably arranged parallel to each other.

With such a parallel arrangement, in a small space, a large number of packages with contact lenses contained therein can be sterilized.

In a further elaboration, hot air can be passed along the packages. The passing hot air provides for an efficient heat transfer to the packages. It is then preferred that the dry hot air flow is a turbulent air flow.

Possibly, the carriers may first be introduced into a closable load lock, while in the load lock, after the carrier has been introduced therein, the temperature and the pressure are adjusted to a desired value. The desired value for the temperature may for instance be higher than approximately 90° C., while the desired value for the pressure may for instance be higher than approximately 2 bar, in particular higher than approximately 3 bar, and preferably higher than approximately 4 bar. Next, the carrier may be moved from the load lock into a carrier receiving chamber where the hot air under excess pressure is continuously present. The order may for instance be such that the temperature outside the package leads to the above-mentioned vapor pressure, and that a minimum pressure (outside the package) follows from the thus given vapor pressure. Preferably, the hot air has a temperature of at least 100° C., and the space is in particular under a pressure that is higher than approximately 2 bar or higher than approximately 3 bar, and is preferably higher than 4 bar.

In an advantageous elaboration, the temperature and the pressure can be controlled independently of each other, whereby temperature and pressure are hence preferably not determined by the vapor pressure as in conventional systems. In a further, advantageous additional elaboration, the pressure only needs to be greater than or equal to the vapor pressure in the package associated with the temperature. The hot air, further, is preferably circulated.

Preferably, a second closable lock is present for receiving from the carrier receiving chamber once-sterilized contact lenses included in packages, whereby the carrier with sterilized contact lens-containing packages is moved from the carrier receiving chamber into the second lock, whereafter the temperature in the second lock is lowered and also the pressure in the second lock is lowered, more specifically at such a rate that the pressure prevailing in the lock is always greater than the pressure prevailing in the package.

In the use of a load lock and an unload lock to introduce the carriers into the carrier receiving chamber and to remove them from it, respectively, the temperature and the pressure in the carrier receiving chamber can be kept at an equal level. The carrier receiving chamber does not need to be regularly heated or cooled but can sterilize packages with lenses in the carriers continuously. As a result, the actual sterilization process is a continuous process and the introduction and removal of the carriers is an intermittent process. Further, in the use of this sterilization process in an in-line system, no intermediate storage of carriers is needed.

In the embodiment of the method with two locks, that is, a load lock and an unload lock, it is further preferred that the heat that is released upon cooling of air contained in the unload lock is used in heating up the air contained in the load lock.

Such a transfer of heat from the unload lock to the load lock saves energy and favors the velocity of the heating process.

The invention provides a first apparatus for sterilizing contact lenses packaged in a moist environment, wherein the apparatus comprises a carrier receiving chamber for receiving a number of carriers in which a number of packaged contact lenses are receivable, wherein a heating device is provided for heating dry air, the apparatus being provided with a control for continuously keeping the hot dry air in the interior of the carrier receiving chamber within a particular temperature and pressure range, the control being arranged to keep the pressure in the carrier receiving chamber superatmospheric.

With such an apparatus, corresponding advantages can be obtained to those described with reference to the method according to the invention. Furthermore, a sterilization apparatus that works with hot air is safer for a user than a sterilization apparatus that works with steam. In case of an incident, hot air causes less severe wounds than heat of condensation released in the use of hot steam.

The invention also provides a second apparatus for sterilizing contact lenses packaged in a moist environment, wherein the apparatus comprises a carrier receiving chamber for receiving a number of carriers in which a number of packaged contact lenses are receivable, wherein a heating device is provided for heating air that may contain steam, wherein at least one lock is provided for receiving therein at least one carrier, the apparatus being provided with a control for continuously keeping the interior of the carrier receiving chamber within a particular temperature range, the control being arranged for controlling at least the temperature in the lock according to a particular path.

With this apparatus, in an efficient manner, semicontinuously, a lens sterilization process can be obtained that is particularly favorable from an energetic point of view. As the temperature in the carrier receiving chamber is kept constant, little energy is lost. Only the space in the at least one lock needs to be heated up and cooled.

These advantages can also be obtained in the first apparatus according to the invention when, in accordance with a further elaboration of the invention, it is provided with at least one lock for receiving therein at least one carrier, the apparatus being provided with a control for controlling at least the temperature and pressure in the at least one lock according to a particular path.

According to a further elaboration of the invention, both the first apparatus and the second apparatus may be provided with a second lock, the one lock being a load lock and the second lock being an unload lock.

According to a further elaboration of the invention, both the first apparatus and the second apparatus may be provided with a heat transfer arranged for transferring heat released at the unload lock to air and carrier to be heated up in the load lock. This heat transfer provides for an energy saving and is favorable for the heat-up velocity of the load lock.

According to a further elaboration of the invention, the carrier receiving chamber can comprise a drum and a carrier frame rotatably arranged therein.

According to a further elaboration of the invention, the drum is provided with at least one opening to which the at least one lock is connected. For a carrier situated in the load lock, this opening can constitute the access to the carrier frame in the drum. Also, for a carrier situated in the carrier frame, the opening can constitute the access to the unload lock.

In a further elaboration of the invention, a circulation device is provided for circulating heated air through the carrier receiving chamber. Circulating hot air promotes an efficient heat transfer between the air and the packages in the carrier receiving chamber.

According to a further elaboration of the invention, the circulation device is arranged for circulating the air in a first direction through the drum, while the carrier frame rotates in a second direction which is opposite to the first direction, so that heating of the packages takes place countercurrently.

In a further elaboration of the invention, the control is arranged for controlling the temperature and the pressure in the carrier receiving chamber independently of each other. This enables optimum setting of the process parameters of temperature and pressure.

Further elaborations of the invention are described in the subclaims and will be further clarified hereinafter with reference to the drawing, wherein:

In the various figures, like reference numerals refer to like parts.

Figure 1:
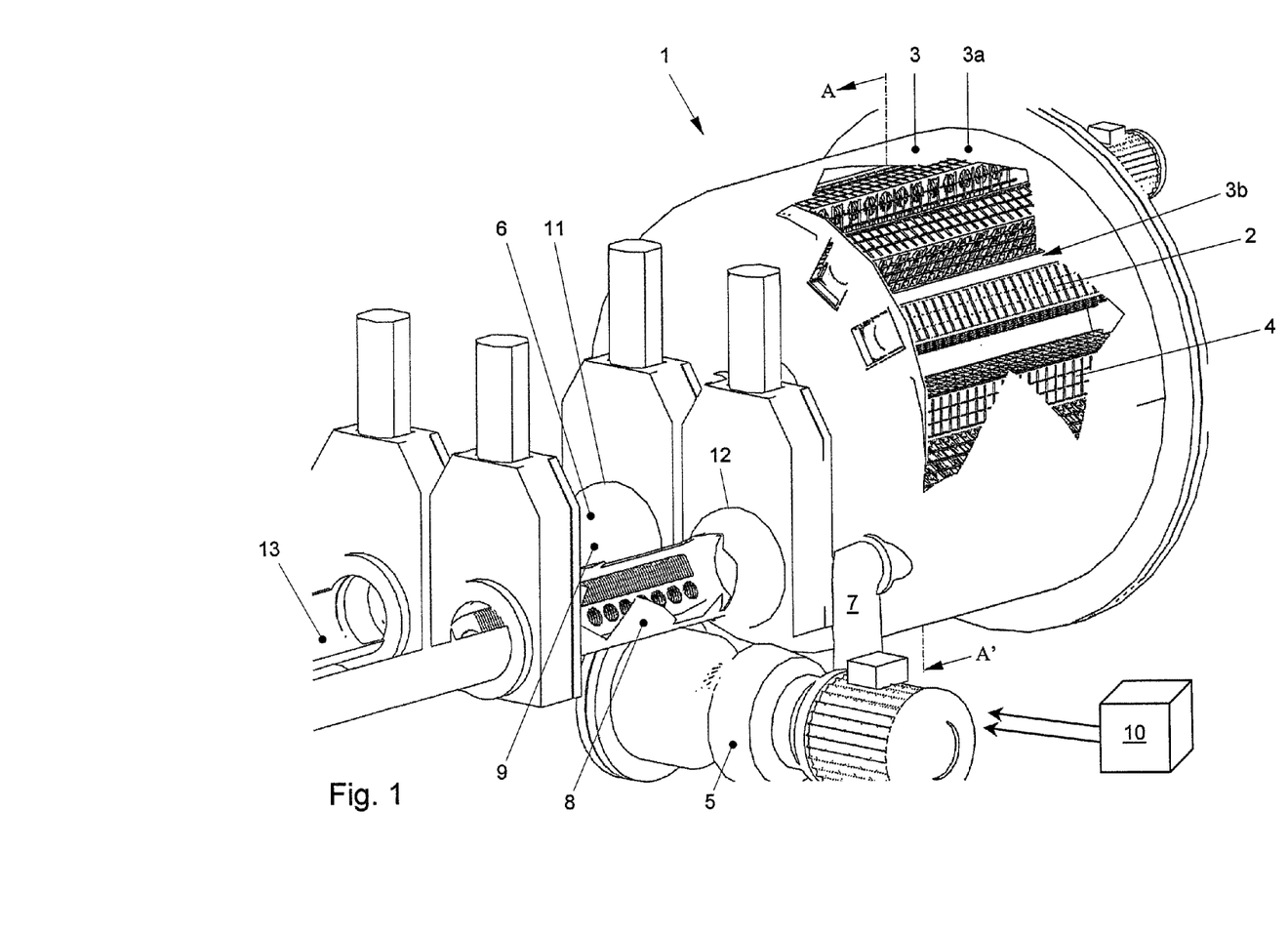
FIG. 1 shows a cutaway perspective view of an apparatus for sterilizing contact lenses.
Figure 2:
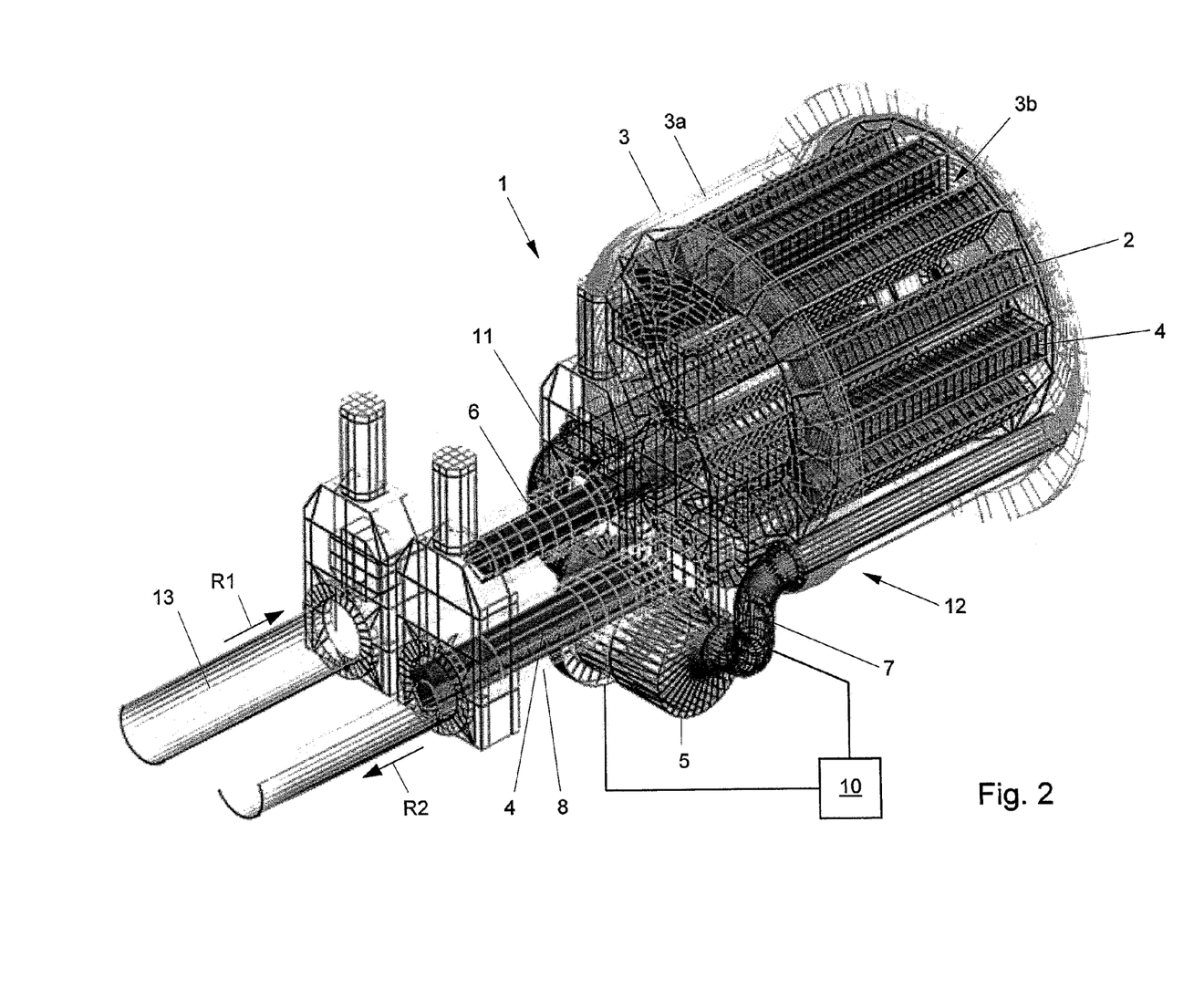
FIG. 2 shows a second cutaway perspective view of an apparatus for sterilizing contact lenses.

In FIG. 1 a cutaway perspective view of an apparatus 1 for sterilizing contact lenses is represented. In FIG. 2 the apparatus 1 from FIG. 1 is represented in a wholly cutaway perspective view. Using this apparatus 1, contact lenses included in a moist environment in a closed package 2 can be sterilized. For this purpose, the package 2 is heated and the heating is carried out by introducing the package 2 into a space that is heated with dry hot air. Sterilization with dry air prevents the package being affected by moisture, which does occur in sterilizing with steam. Further, a sterilization apparatus that works with hot air is safer for a user than a sterilization apparatus that works with steam. In case of an incident, hot air causes less serious wounds than heat of condensation released in the use of hot steam.

Figure 6:
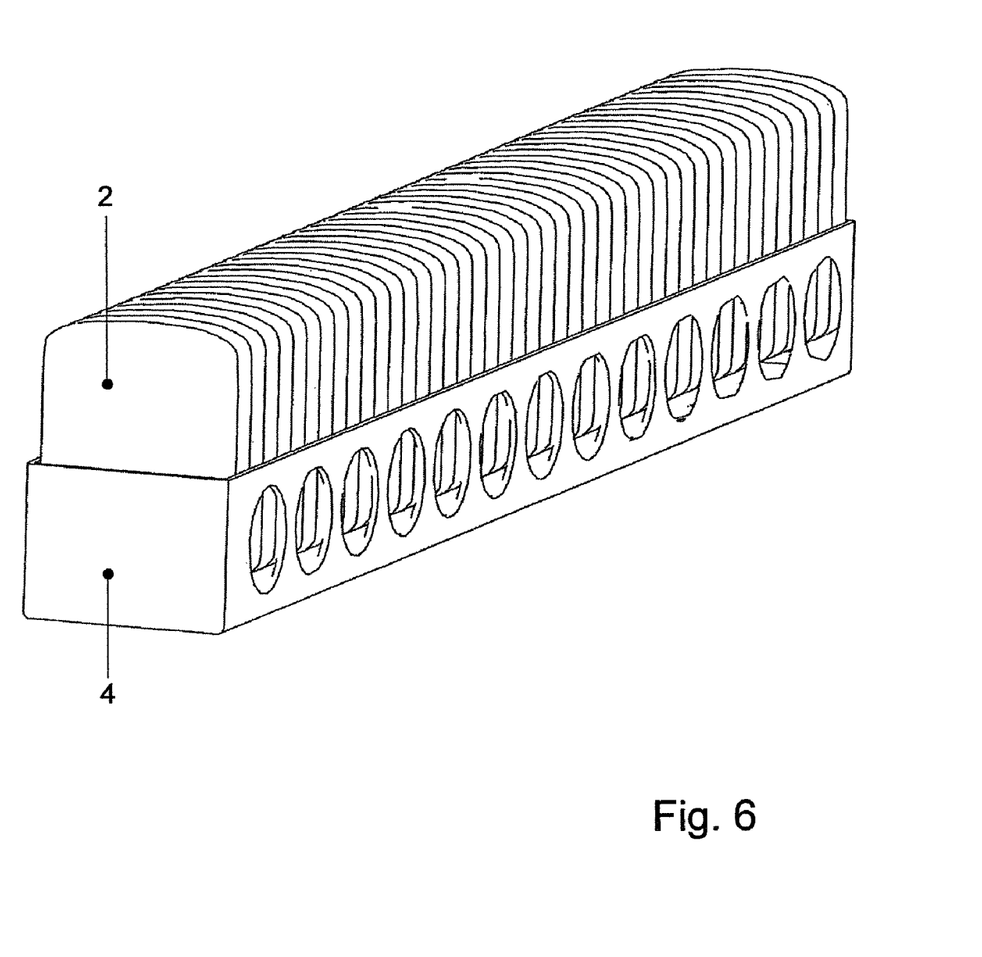
FIG. 6 shows a perspective view of a carrier.

The space may already be at a superatmospheric pressure or may be adjusted to a superatmospheric pressure. To be able to accomplish this, the apparatus 1 comprises a carrier receiving chamber 3, for instance a sterilization tank provided with a drum 3a, for instance a pressure vessel, and a carrier frame 3b, rotatably arranged therein, for receiving a number of carriers 4 in which a number of packages 2 with contact lenses are receivable. A package can for instance comprise a hard plastic lower part and be closed with a closure of aluminum foil. It is also possible that a package is made wholly of a flexible material. An example of a carrier 4 is shown in FIG. 6. This carrier 4 can for instance be a lightweight carrier.

The apparatus 1 further has a heating device 5 for heating the dry air. A control 10 (shown schematically in FIGS. 1 and 2) keeps the hot dry air continuously within a particular temperature and pressure range in the interior of the drum 3a.

The carrier receiving chamber 3 may already be heated and have a temperature of 120°-130° C. The heating of the carrier receiving chamber 3 can for instance be done using an insulated resistance wire wound around the drum 3a. Also, the carrier receiving chamber 3 may be heated by hot air, but other heating means are options as well. Preferably, the carrier receiving chamber 3 is insulated, so that heat is lost to the least possible extent. The heating device 5 needs to keep the hot air present in the interior of the drum 3a at a desired temperature only by supplementarily heating the air off and on. The control 10 is further arranged for keeping the pressure superatmospheric. Preferably, the superatmospheric pressure is kept above the pressure prevailing in the package 2, for instance at approximately 3 bar.

For sterilizing the contact lenses in the closed packages 2, the packages 2 are placed in the carriers 4 in parallel arrangement (see FIG. 6) and so brought into the carrier frame 3b rotatably arranged in the drum 3a. Rotation of the carrier frame 3b can be effected by means of one or more magnetic couplings. The carriers 4 with packages 2 are first introduced into a closable lock, the load lock 6. When a carrier 4 is in the load lock 6, in the lock 6 the pressure and the temperature are adjusted to a desired value. The pressure in the lock is adjusted to a value equal to that prevailing in the drum 3a. The temperature in the lock is adjusted to approximately 90° C. A further explanation on this will follow hereinafter with reference to FIG. 5. For this purpose, the apparatus 1 utilizes the control 10 which controls the temperature and the pressure in the lock 6 according to a particular path. When those values have been reached, the load lock 6 is opened and the carrier 4 is moved from the load lock 6 into the carrier receiving chamber 3 through an opening 11 in the drum 3a. By means of a magnetic feed-through, the carrier 4 is moved in direction R1 to the carrier frame 3b in the drum 3a. In the drum 3a, the hot air under excess pressure, as discussed earlier, is present continuously.

Figure 3:
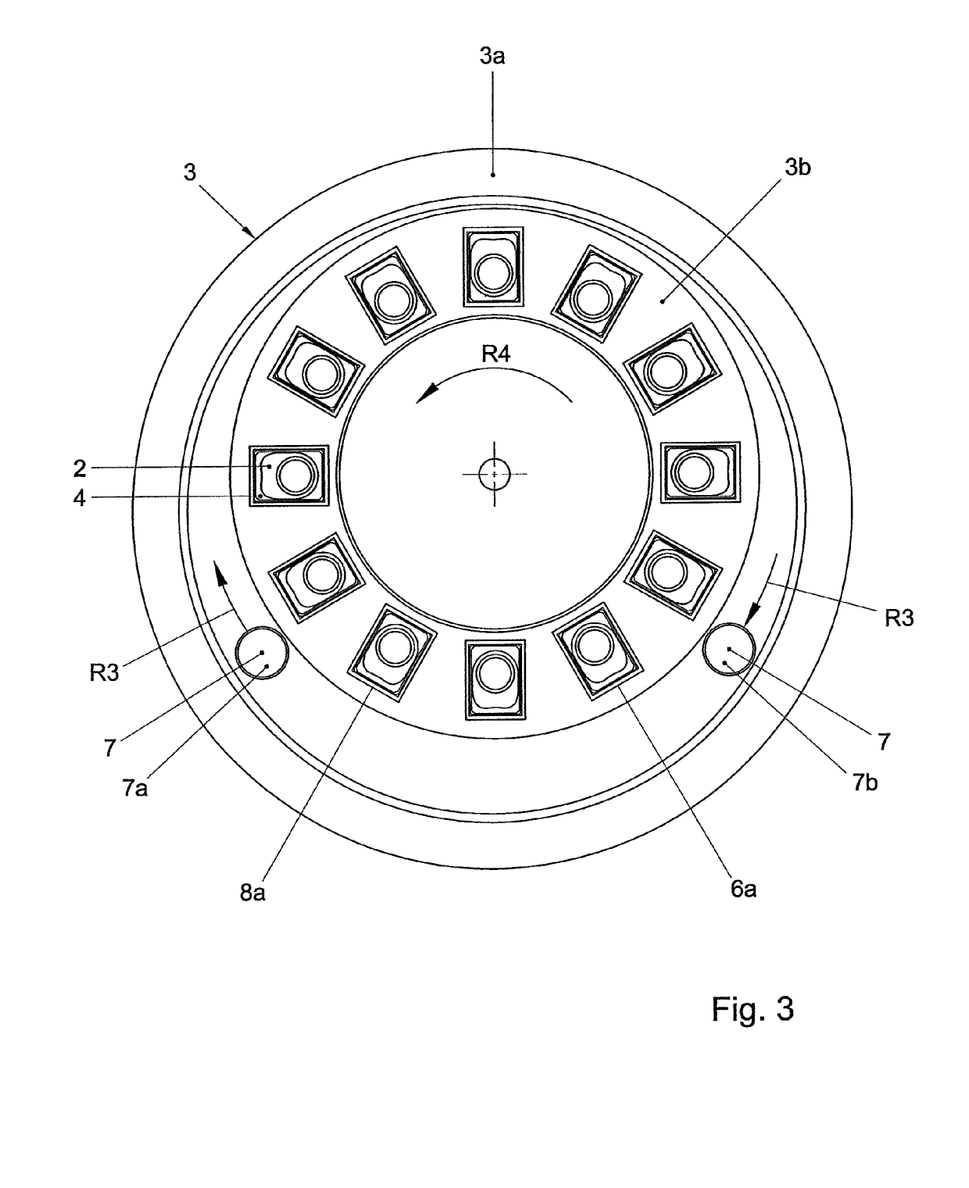
FIG. 3 shows a cross section of the apparatus along the line A-A' as indicated in FIG. 1.

FIG. 3 shows a cross section of a carrier receiving chamber 3. It is clear to see that the apparatus 1 comprises a circulation device 7, for instance provided with one or more fans, which is driven by means of a magnetic clutch. The circulation device 7 provides for circulation of the hot air that is present in the drum 3a of the carrier receiving chamber 3. The circulation device 7 circulates the dry hot air from the air supply 7a in a first direction R3 through the drum 3a to the air discharge 7b. At the same time, the carrier frame 3b rotates in a second direction R4 which is opposite to the first direction R3. The carriers 4 are introduced in the carrier frame 3b in the carrier receiving chamber 3 at a first location 6a. After sterilizing, the carriers leave the carrier frame 3b and the carrier receiving chamber 3 at a second location 8a. Evidently, these locations may be provided at different places in the carrier receiving chamber 3, but the input and output locations may also coincide when, for instance, the load lock and the unload lock are arranged in line with each other on opposite sides of the carrier receiving chamber 3. Further, the first direction R3 and the second direction R4 may also be opposite to the directions indicated in the figure. As a result, the dry hot air is passed along the packages 2, so that these are heated countercurrently and an efficient heat transfer is achieved. The control 10 (see FIGS. 1 and 2) is further arranged for controlling the temperature and the pressure in the carrier receiving chamber 3 independently of each other. Through the presence of liquid in the packages 2, steam is formed in the packages 2, so that the sterilization of the contact lenses takes place in the packages 2. As in the carrier receiving chamber 3 a superatmospheric pressure prevails that is higher than the pressure in the package 2, the package 2 will not swell as a result of the steam formation, and tearing open of the package 2 is avoided. The dry hot air that is present around the packages 2 does not contain any steam, so that the typically aluminum packages are not affected thereby.

After sterilization of the contact lenses included in the packages 2, the carriers 4 are moved from the carrier frame 3b out of the carrier receiving chamber 3 using a magnetic feed-through in direction R2 into the unload lock 8. The opening 12 of the unload lock 8 on the side of the carrier receiving chamber 3 is closed and then the temperature and the pressure in the second lock 8 are lowered. This lowering proceeds at such a rate that the pressure prevailing in the unload lock 8 is always greater than the pressure prevailing in the package. Here too, the control 10 controls the lowering of pressure and temperature according to a particular path. In this way, the packages 2 remain whole during the cooling process. The unload lock 8 may be actively cooled by passing cold air along it.

The apparatus 1 has a heat transfer 9 between the load lock 6 and the unload lock 8. The heat transfer 9 provides that heat released upon cooling of the air present in the unload lock 8 is used in heating up the air present in the load lock 6. As a result, the energy is utilized efficiently and the heat-up process in the load lock 6 proceeds faster.

The apparatus 1 further comprises process integration means, so that the apparatus 1 can form part of a semicontinuous process. For instance, sterilization of the contact lenses included in packages 2 can be part of a process in which contact lenses are manufactured, packaged and then sterilized. Other process steps can also be options. The sterilization process step which is carried out using the apparatus 1 according to the invention is relatively short in that the apparatus effects a short heat-up and cool-off period of the individual carriers. The carriers leave the sterilization apparatus at regular short intervals and may traverse any subsequent process steps. When the sterilization apparatus is used in-line, no intermediate storage of the carriers is needed.

Figure 4:
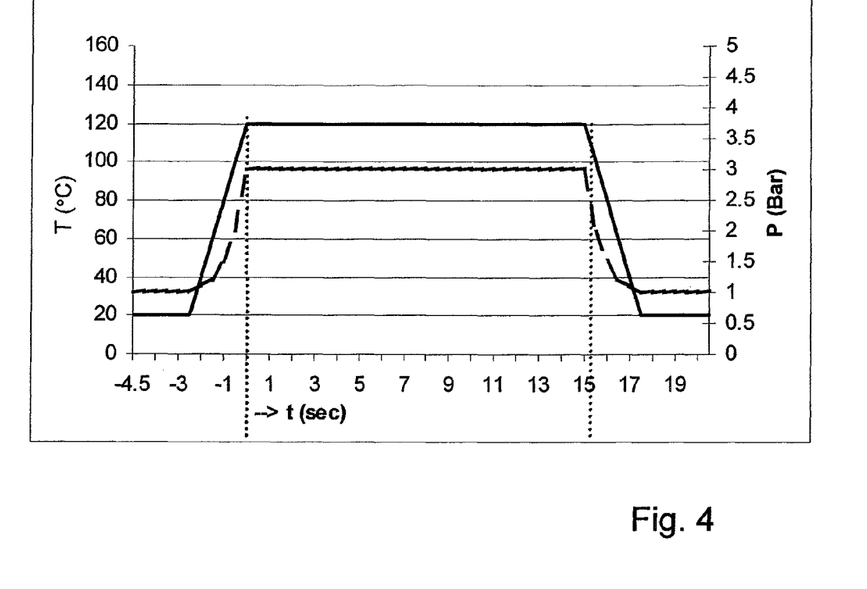
FIG. 4 shows a diagram representing the autoclave sterilization process according to the prior art.
Figure 5:
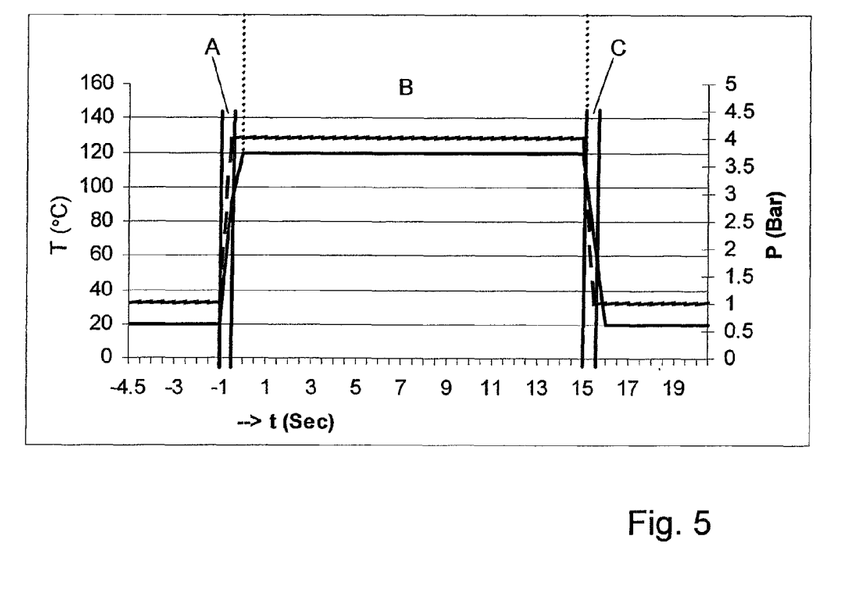
FIG. 5 shows a diagram representing the sterilization process according to an exemplary embodiment of the invention.

In clarification of the sterilization process according to the invention, FIG. 4 reflects the sterilization process in an autoclave according to the prior art and FIG. 5 reflects the sterilization process according to an exemplary embodiment of the invention.

In FIGS. 4 and 5, the horizontal axis and the vertical axis plot time and pressure/temperature, respectively. In FIG. 4, the sterilization of a batch of packages is shown. A batch of packages is placed in an autoclave at t=−4.5. Then the autoclave including packages is heated from room temperature to approximately 120° C. and the pressure is raised from atmospheric pressure (1 bar) to a pressure of approximately 3 bar. At t=0 this situation has been reached, and the actual sterilization of the products in the packages begins. At t=15 cooling and lowering of the pressure in the autoclave begin, and at t=17 the batch of packages leaves the autoclave, that is, approximately 20 minutes after placement of the batch in the autoclave. At t=21 the initial situation has been reached and a next batch can be introduced into the autoclave. This cycle of approximately 25 minutes repeats itself with each next batch of products to be sterilized.

In FIG. 5, the carrier receiving chamber is constantly at a temperature of approximately 120° C. and at a pressure of approximately 4 bar. At t=−1, a carrier is introduced from a surroundings into the load lock. The lock closes and the pressure in the lock is raised over a period A from atmospheric pressure (1 bar) to a pressure of approximately 4 bar. Also, the temperature in the load lock is raised to 90° C. At t=0 the first carrier is placed from the load lock into the carrier frame in the carrier receiving chamber and the sterilization process for this carrier begins. After a period B, when t=15 has been reached, this carrier is placed in the unload lock, in which an equal pressure to that in the drum prevails, and the pressure reduction and cooling of the unload lock begins until after a period of time C atmospheric pressure and approximately room temperature have been reached. The first carrier leaves the sterilization apparatus after approximately 16.5 minutes.

Meanwhile, at t=0+x a next carrier is placed from the surroundings into the carrier receiving chamber, followed by a third at t=0+2x, and so forth. These carriers each leave the sterilization apparatus likewise after approximately 16.5 minutes in the same manner as the first carrier as described above. It will be clear that this can go on indefinitely, since the properties in the carrier receiving chamber are substantially constant and remain so.

It will be clear that the invention is not limited to the exemplary embodiment described, but that various modifications within the scope of the invention as defined by the claims are possible. An apparatus such as described hereinabove is, for instance, also suitable for sterilizing contact lenses packaged in a moist environment while the hot air in the carrier receiving chamber may contain steam. For this purpose, the apparatus comprises a carrier receiving chamber for receiving a number of carriers in which a number of packaged contact lenses are receivable, while a heating device is provided for heating air that may contain steam, while at least one lock is provided with a control for keeping the interior of the carrier receiving chamber continuously within a particular temperature range, the control being arranged for controlling at least the temperature in the lock according to a particular path. This apparatus is suitable for sterilizing contact lenses included in packages not sensitive to corrosion. This apparatus, further, may also be used in a semicontinuous sterilization process and may comprise the same parts as those described for the apparatus in the exemplary embodiment and afford the same effects.

Further, it is possible that several carriers can be introduced simultaneously into the load lock or the unload lock of the apparatus according to the invention. It is also possible that the carrier receiving chamber is designed in a different manner and that the carriers are included in the carrier frame in a different manner. It is also possible that the carriers are passed on from the load lock to the carrier receiving chamber using a different feed-through. The same holds for the transit of the carriers from the carrier receiving chamber to the unload lock.

The invention claimed is:

1. A method for sterilizing new contact lenses included in a moist environment in a sealed lens package, comprising:
    loading a plurality of the sealed lens packages into a carrier;
    heating each lens package via an automated introduction of the loaded carrier into a space which is heated with dry hot air;
    rotating the loaded carrier in a first rotational direction within the space which is heated with dry hot air on a rotatable carrier frame disposed within the space.

2. The method according to claim 1, wherein the space is at a superatmospheric pressure or is adjusted to a superatmospheric pressure.

3. The method according to claim 2, wherein the superatmospheric pressure is kept above a pressure prevailing in the package.

4. The method according to claim 2, wherein the pressure is kept at approximately 3 bar.

5. The method according to claim 1, wherein the plurality of sealed lens packages is arranged parallel to each other in the loaded carrier.

6. The method according to claim 1, wherein the dry hot air is passed along the plurality of the sealed lens packages in a circulation direction that is opposite the first rotational direction.

7. The method according to claim 6, wherein the dry hot air flow is a turbulent air flow.

8. The method according to claim 1, wherein the loaded carrier is first introduced into a first closable load lock, wherein in the first closable load lock, after the loaded carrier has been introduced therein, a pressure and a temperature are adjusted to a desired value.

9. The method according to claim 8, wherein the temperature in the first closable load lock is higher than approximately 90° C., wherein the pressure in the first closable load lock is higher than approximately 4 bar.

10. The method according to claim 8, further comprising:
    moving the loaded carrier from the first closable load lock into the space which is heated with dry hot air via a magnetic feed,
    wherein the space which is heated with dry hot air is a carrier receiving chamber including a drum rotatably housing the rotatable carrier frame, and
    where the hot dry air in the drum is continuously maintained under excess pressure during operation.

11. The method according to claim 10, further comprising:
    transferring the loaded carrier from the carrier receiving chamber to a closable unload lock; and
    lowering a temperature and a pressure in the closable unload lock at such a rate that the pressure prevailing in the second, closable unload lock is always greater than the pressure prevailing in the plurality of sealed lens packages.

12. The method according to claim 11, further comprising transferring via a heat exchanger the heat that is released upon cooling of air present in the closable unload lock to the first closable load lock.

13. The method according to claim 8, wherein the temperature and the pressure in the first closable load lock are controlled independently of each other.

14. The method according to claim 1, wherein the dry hot air has a temperature of at least approximately 100° C., and wherein the space is under a pressure that is higher than approximately 4 bar.

15. The method according to claim 1, wherein the dry hot air is circulated around the loaded carrier.

* * * * *